United States Patent

Omura

Patent Number: 5,525,605
Date of Patent: Jun. 11, 1996

[54] REMEDY FOR INFLAMMATORY INTESTINAL DISEASES

[75] Inventor: Shigeki Omura, Tokyo, Japan

[73] Assignee: Tokyo Tanabe Company Limited, Tokyo, Japan

[21] Appl. No.: 360,825

[22] PCT Filed: Jul. 26, 1993

[86] PCT No.: PCT/JP93/01044

§ 371 Date: Dec. 21, 1994

§ 102(e) Date: Dec. 21, 1994

[87] PCT Pub. No.: WO94/03172

PCT Pub. Date: Feb. 17, 1994

[30] Foreign Application Priority Data

Jul. 30, 1992 [JP] Japan ............... 4-203636

[51] Int. Cl.$^6$ ............... A61K 31/505; A61K 9/48; A61K 9/20

[52] U.S. Cl. ............... 514/258; 424/451; 424/464

[58] Field of Search ............... 544/282; 514/258, 514/886; 424/451, 464

[56] References Cited

U.S. PATENT DOCUMENTS 4,816,459  3/1989  Matsuishi et al. ............... 514/258

FOREIGN PATENT DOCUMENTS 183581  7/1988  Japan .
243082  10/1988  Japan .

*Primary Examiner*—John W. Rollins
*Attorney, Agent, or Firm*—McGlew and Tuttle

[57] ABSTRACT

A remedy for inflammatory intestinal diseases which contains as the active ingredient 9-(4-acetyl-3-hydroxy-2-n-propylphenoxymethyl)-3-(1H-tetrazol-5-yl)-4H-pyrido[1,2-a]pyrimidine-4-one represented by the formula:

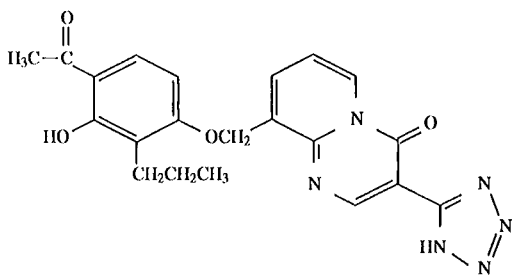

or a physiologically acceptable salt thereof. The compound specified in the present invention can remedy not only inflammatory responses caused in inflammatory intestinal diseases in a short time but also remove the symptoms deriving from digestive organs, which are caused together with the inflammatory response of the intestine.

9 Claims, No Drawings

REMEDY FOR INFLAMMATORY INTESTINAL DISEASES

FIELD OF THE INVENTION

The present invention relates to a remedy for inflammatory intestinal diseases which contains as the active ingredient 9-(4-acetyl-3-hydroxy-2-n-propylphenoxymethyl)-3-(1H-tetrazol-5-yl)-4H-pyrido[1,2-a]pyrimidine-4-one (hereinafter referred to as Compound 1) or a physiologically acceptable salt thereof.

BACKGROUND ARTS

Inflammatory intestinal diseases are spontaneous and chronic diseases of which typical examples are ulcerative colitis and Crohn's disease, and the numbers of the patients suffering therefrom have been steadily increasing in recent years. Many principal and clinical investigations have been vigorously carried out by investigating groups such as the special diseases investigating group on refractory inflammatory intestinal disorders of the Ministry of Health, Japan; however, the cause and the morbidity of the diseases involved have not been discovered.

For the treatment of inflammatory intestinal diseases, only several attempts such as the administration of an immuno-suppressive agent, 6-mercaptopurine, the voluminous administration of an antibacterial agent, sulfasalazine, and oral, intravenous, topical and intracolonic administration of steroid hormones, such as prednisolone acetate, have been made. However, these pharmaceutical treatments can play a role only as symptomatic therapy for the diseases and are not of the type which can quickly remove the symptoms arising from digestive organs, such as diarrhea, bloody stool, and abdominal pain. Furthermore, these drugs mentioned above give side effects in a high rate and are required to be administered voluminously for a long period, and therefore, such drugs have a disadvantage in terms of the maintenance of the quality of life of the patients. Moreover, it is known that non-steroid anti-inflammatory agents such as indomethacin, which is commonly used for the treatment for inflammatory diseases, normally make the condition of the patients suffering from the inflammatory intestinal diseases worse, providing difficulty in the maintenance of remission of the diseases.

It is an object of the present invention to remedy inflammatory reactions, which is the cause of the disease, in a short time and to provide a highly safe remedy for the inflammatory intestinal diseases by removing the symptoms deriving from digestive organs, such as diarrhea, bloody stool, and abdominal pain, therewith.

DISCLOSURE OF THE INVENTION

In the course of pharmacological study on pyridopyrimidine compounds known as having suppressive action on the central nervous system (Japanese Patent Laid-opened No. Sho 49-14495 Gazette), suppressive action on allergic reaction (Japanese Patent Laid-opened No. Sho 54-36294 Gazette) and antagonistic action on SRS-A (Japanese Patent Laid-opened No. Sho 62-24262 Gazette and No. Sho 63-183581 Gazette), the inventors of the present patent application found that either compound 1 represented by the formula:

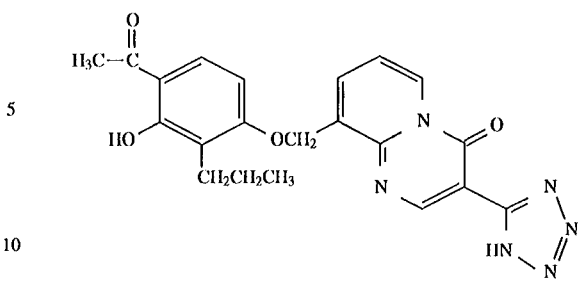

or a physiologically acceptable salt thereof (hereinafter referred to as Pyridopyrimidine compound I) has remedial action on inflammatory intestinal diseases, which has not been known in the past, and thereby accomplishing the present invention.

The compound 1, the active ingredient specified in the present invention, can be prepared, for example, by forming a tetrazol ring in reacting 9-(4-acetyl-3-hydroxy-2-n-propylphenoxymethyl)-3-cyano-4H-pyrido[1,2-a]pyrimidine-4-one with aluminium azide, then converting the resulting compound to a potassium salt thereof by using potassium hydroxide/ethanol solution and letting it precipitate by neutralizing it with chloric acid or sulfuric acid.

For the physiologically acceptable salt of the compound 1, a sodium or potassium salt thereof can be exemplified.

The compound 1 showed distinct remedial effect on intestinal impairment when it was administered into guinea pigs having intestinal impairment which was induced by the intracolonic injection of acetic acid (intestine-impaired guinea pigs), or rats and mice both having intestinal impairment which was induced by letting them freely drink dextran sodium sulfate solution. Thus it was demonstrated that the compound 1 is useful as a remedy for inflammatory intestinal diseases.

The remedy for inflammatory intestinal diseases specified in the present invention can be administered orally or non-orally, and the dosage for use may be determined depending upon age, symptom, body weight and sex of the patients, etc. In general, the dosage per day of the active ingredient, pyridopyrimidine compound I, is preferably in a range from 1 mg to 25 g, more preferably from 5 mg to 5 g, for oral administration, and is from 0.1 mg to 10 g, more preferably from 1 mg to 4 g, for non-oral administration. Within the dose range presented above, it is preferable to take the remedy from 1 to 8 times per day, more preferably from 1 to 4 times per day, by dividing the dosage.

The remedy for inflammatory intestinal diseases specified in the present invention includes various pharmaceutical compositions in which physiologically acceptable solid or liquid carriers are combined with the active ingredient, pyridopyrimidine compound I, subject to maintaining the range of the dosage per day as mentioned above. For such pharmaceutical compositions, tablets, pills, capsules, powders, fine granules, granules, solutions, medicated syrup, suspensions, emulsions, injections and enteric coated preparations can be exemplified. For the carriers, any carriers normally used for such formulations can be used, which include fillers, binders, disintegrators, lubricants, protectives, solubilizing agents, emulsifiers, suspending agents, stabilizers, various solvents, adequate perfumes, etc.

BEST MODE FOR CARRYING OUT THE INVENTION

Now, the present invention is further explained with reference to Examples and Examples for pharmaceutical preparations.

EXAMPLE 1

(Test for remedying inflammatory intestinal disorders)

5 to 15 male Hartley-strain guinea pigs weighing 400 to 450 g were used for one test group, and the remedial effect on intestinal diseases induced by the intracolonic injection of acetic acid was examined in a manner of oral administration for the test compounds. As the test compounds, Compound 1, sulfasalazine and the steroid hormone, prednisolone acetate, were provided. The test compound was applied to each guinea pig beforehand, and 3% acetic acid solution was then injected intracolonically at a volume of 1.5 ml/body to induce the intestinal diseases. Three hours later following the intracolonic injection of acetic acid, Evans' blue was applied to the animal intravenously at a rate of 36 mg/Kg. One hour later, the animal was sacrificed by decapitaion, and the intestine was then removed from the animal to determine the quantity of Evans' blue that leaked into the intestine according to the method of Katayama et al. (Microbiology and Immunology Vol. 22, pp. 89, 1978). Namely, the intestine removed was cut into small pieces and 2 ml of 1-N solution of potassium hydroxide was added thereto, then the solution was allowed to stand at 37° C. overnight, added to 18 ml of a mixture of 0.6-N phosphoric acid solution and acetone (mixing ratio, 5:13) to extract the dye. The extract was centrifuged at 3,000 r.p.m. for 15 min. to thereby obtain the supernatant. By determining the absorbance of the supernatant at 620 nm, the amount of the dye leaked was calculated. The test compound was applied once a day for three days, then the administration of acetic acid via the intestine was conducted 4 hours later following the last administration of the test compound. The results are shown in Table 1. The control group in the table represents a group to which only acetic acid was administered and the test compound was not applied.

TABLE 1

Effect on Inflammatory Intestinal Disease of Guinea Pigs Induced by Acetic Acid.

| Test Compound | Dose (mg/Kg) | Remedial Effect on Inflammatory Intestinal Diseases Amount of Dye Leaked (ug/Tissue) |
|---|---|---|
| Control Group | — | 190.7 ± 13.2 |
| Compound 1 | 3 | 151.2 ± 10.8* |
|  | 10 | 122.5 ± 15.9** |
|  | 30 | 128.0 ± 8.4** |
|  | 100 | 120.9 ± 8.9** |
| Sulfasalazine | 10 | 147.9 ± 29.4 |
|  | 100 | 213.2 ± 13.3 |
| Prednisolone Acetate | 10 | 192.6 ± 18.1 |

Mean ± S.E.
*p < 0.05
**p < 0.01

The remedial effect of the compound 1 on inflammatory intestinal diseases was shown with significant differences, which was apparently superior to the effect of sulfasalazine or prednisolone acetate.

EXAMPLE 2

(Test for evaluating remedial effect on inflammatory intestinal diseases)

6 male Hartley-strain guinea pigs weighing 400 to 450 g were used for one test group, and the remedial effect on intestinal diseases induced by the intestinal injection of acetic acid was examined in a manner of oral administration for the test compounds. As the test compound, Compound 1 was provided. The test compound was applied to each guinea pig beforehand, and 3% acetic acid solution was then injected through the intestine at a volume of 1.5 ml/body to induce the intestinal diseases. At 24 and 48 hours after the intestinal injection of acetic acid, a colon of the guinea pig injected was removed, then the areas of ulcer and erosion which are induced by the intestinal injection of acetic acid were measured by using a two dimentional image analyzer(nexusQube; trademark Nexus Inc.). The test compound was applied once a day for three days, then the injection of acetic acid via the intestine was conducted 4 hours later following to the last administration of the test compound. As shown in Tables 2 and 3, the compound 1 showed remedial effect on inflammatory intestinal diseases with significant differences.

TABLE 2

Effect on Inflammatory Intestinal Disease of Guinea Pigs Induced by Acetic Acid. - At 24 hours after Intestinal Injection of Acetic Acid -

| Test Compound | Dose (mg/Kg) | Remedial Effect on Inflammatory Intestinal Diseases Area of Ulcer (mm$^2$) |
|---|---|---|
| Control Group | — | 457.7 ± 83.9 |
| Compound 1 | 100 | 120.2 ± 76.5* |

Mean ± S.E.
*p < 0.05

TABLE 3

Effect on Inflammatory Intestinal Disease of Guinea Pigs Induced by Acetic Acid. - At 48 hours after Intestinal Injection of Acetic Acid -

| Test Compound | Dose (mg/Kg) | Remedial Effect on Inflammatory Intestinal Diseases Area of Ulcer (mm$^2$) |
|---|---|---|
| Control Group | — | 316.0 ± 105.9 |
| Compound 1 | 100 | 44.3 ± 17.5* |

Mean ± S.E.
*p < 0.05

EXAMPLE 3

(Test for evaluating remedial effect on inflammatory intestinal diseases)

3 to 7 male 8 weeks old SD-strain rats were used for one test group, and the remedial effect of the test compounds on intestinal diseases induced by free drinking of 5% dextran sodium sulfate (molecular weight 25,000; manufactured by Tokyo Kasei Kogyo Co., Ltd.) was examined in a manner of oral administration. Compound 1 was provided as the test compound. Water containing 5% dextran sodium sulfate was given to each rat for 7 days to thereby induce intestinal diseases in the rat.

The test compound was applied to the rat once a day simultaneously with the drinking of water containing 5% dextran sodium sulfate for 7 days. On the next day after the last administration of the test compound, a colon of the rat was removed to measure the weight increase of the colon induced by free drinking water containing 5% dextran sodium sulfate. The results are shown in Table 4.

In the table, the no-treatment group represents a group to which neither 5% dextran sodium sulfate nor the test compound were applied, namely a group of normal rats, and the control group represents a group which freely took water containing 5% dextran sodium sulfate but not the test compound.

TABLE 4

Effect on Inflammatory Intestinal Disease of Rats Induced by Dextran Sodium Sulfate

| Test Compound | Dose (mg/Kg) | Remedial Effect on Inflammatory Intestinal Diseases Weight of Colon (g) |
|---|---|---|
| No-treatment Group | — | 1.74 ± 0.02** |
| Control Group | — | 2.12 ± 0.06 |
| Compound 1 | 10 | 1.93 ± 0.09 |
|  | 30 | 1.94 ± 0.02* |
|  | 100 | 1.94 ± 0.04* |

Mean ± S.E.
*$p < 0.05$
**$p < 0.01$ (compared with control group)

As can be seen from the table, compound 1 showed remedial effect on intestinal diseases with significant differences.

EXAMPLE 4

(Test for evaluating remedial effect on inflammatory intestinal diseases)

4 to 6 female 9 weeks old CBA/J-strain mice were used for one test group, and the remedial effect of the test compounds on intestinal diseases induced by free drinking of water containing 5% dextran sodium sulfate was examined in a manner of oral administration. Compound 1 was provided as the test compound. Water containing 5% dextran sodium sulfate was given to each mouse for 50 days to thereby induce intestinal diseases in each mouse.

The test compound was applied to each mouse once a day simultaneously with the drinking of water containing 5% dextran sodium sulfate for 50 days. On the next day after the last administration of the test compound, a colon of the mouse was removed, measuring the length of the colon, to thereby evaluate the effect of the test compound on the shortening of the colon length resulting from the inflammatory response induced by the free drinking of water containing 5% dextran sodium sulfate (Okayasu I., et al.; Gastroenterology Vol. 98, pp. 694–702, 1990). In addition, the effect of sulfasalazine was also evaluated according to the same procedure as used in this test. The results are shown in Table 5 for compound 1, and Table 6 for sulfasalazine.

TABLE 5

Effect on Inflammatory Intestinal Disease of Mice Induced by Dextran Sodium Sulfate

| Test Compound | Dose (mg/Kg) | Remedial Effect on Inflammatory Intestinal Diseases Length of Colon (cm) |
|---|---|---|
| No-treatment Group | — | 7.90 ± 0.24** |
| Control Group | — | 6.13 ± 0.08 |
| Compound 1 | 3 | 6.43 ± 0.10* |
|  | 10 | 6.87 ± 0.17** |
|  | 30 | 6.95 ± 0.16** |

TABLE 5-continued

Effect on Inflammatory Intestinal Disease of Mice Induced by Dextran Sodium Sulfate

| Test Compound | Dose (mg/Kg) | Remedial Effect on Inflammatory Intestinal Diseases Length of Colon (cm) |
|---|---|---|

Mean ± S.E.
*$p < 0.05$
**$p < 0.01$ (compared with control group)

In the table, the no-treatment group represents a group to which neither 5% dextran sodium sulfate nor the test compound were applied, namely a group of normal mice, and the control group represents a group which freely took water containing 5% dextran sodium sulfate but not the test compound.

TABLE 6

Effect on Inflammatory Intestinal Disease of Mice Induced by Dextran Sodium Sulfate

| Test Compound | Dose (mg/Kg) | Remedial Effect on Inflammatory Intestinal Diseases Length of Colon (cm) |
|---|---|---|
| No-treatment Group | — | 8.32 ± 0.24** |
| Control Group | — | 5.08 ± 0.13 |
| Sulfasalazine | 30 | 5.35 ± 0.16 |

Mean ± S.E.
**$p < 0.01$ (compared with control group)

As can be seen from the tables, compound 1 showed remedial effect on intestinal diseases with significant differences, but sulfasalazine did not.

EXAMPLE 5

(Acute Toxicity Test)

The acute toxicity ($LD_{50}$) of compound 1 was evaluated with male ddY mice and SD-strain rats, both of which were 5 weeks old. The $LD_{50}$ of compound 1 on mice was found to be greater than 4.0 g/Kg by oral administration and greater than 100 mg/Kg by intravenous injection. On the other hand, the $LD_{50}$ of compound 1 on rats was greater than 4.0 g/Kg by oral administration and greater than 200 mg/Kg by intravenous injection.

EXAMPLE 6

(Preparation of Tablets)

Example for Pharmaceutical Preparation 1 (Tablets)

|  | % by weight |
|---|---|
| 1) Compound 1 | 10.0 |
| 2) Lactose | 56.0 |
| 3) Corn starch | 15.0 |
| 4) Crystalline cellulose | 15.0 |
| 5) Hydroxypropylcellulose | 3.0 |
| 6) Magnesium stearate | 1.0 |
|  | 100.0 |

All components from 1) to 5) above were mixed, added to water for making the mixture granular, and then subjected to drying. After preparing the shape of the granules obtained to render them uniform, adding the material 6) thereto and mixing it therewith, then the resulting mixture was formed under pressure into tablets having a weight of 100 mg/tablet.

EXAMPLE 7

(Preparation of Capsules)

| Example for Pharmaceutical Preparation 2 (Capsules) | |
|---|---|
| | % by weight |
| 1) Compound 1 | 10.0 |
| 2) Lactose | 65.5 |
| 3) Corn starch | 20.0 |
| 4) Hydroxypropylcellulose | 3.0 |
| 5) Light anhydrous silicic acid | 0.5 |
| 6) Magnesium stearate | 1.0 |
| | 100.0 |

According to a customary method, all components from 1) to 6) were mixed to prepare granules. The granules were then filled into capsules to prepare granules having a weight of 100 mg/capsule.

INDUSTRIAL USE

As explained above, it has been found herein that compound 1 possesses a good remedial effect on inflammatory intestinal diseases, and the effect is superior to those acquired by sulfasalazine and prednisolone acetate. The corresponding pharmaceutical composition containing pyridopyrimidine compound 1 as the active ingredient can be utilized as a remedy for inflammatory intestinal diseases.

What is claimed is:

1. Method for remedial treatment of the symptoms of inflammatory intestinal disease in a patient suffering therefrom, which comprises administering to such patient an effective amount of the active compound 9-(4-acetyl-3-hydroxy-2-n-propyl-phenoxymethyl)- 3-(1-H-tetrazol-5-yl)-4H-pyrido[1,2-a]pyrimidine-4-one of the formula

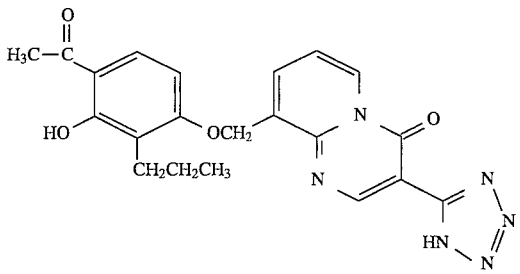

or a physiologically acceptable salt thereof.

2. Method of claim 1 wherein the salt is a sodium or potassium salt.

3. Method of claim 1 wherein the compound is administered in an oral dosage of about 1 mg to 25 g per day.

4. Method of claim 1 wherein the compound is administered in a non-oral dosage of about 0.1 mg to 10 g per day.

5. Method of claim 1 wherein the compound is administered in the form of a pharmaceutical composition together with a physiologically acceptable carrier.

6. Method of claim 5 wherein the composition is in solid form.

7. Method of claim 5 wherein the composition is in tablet form.

8. Method of claim 5 wherein the composition is in capsule form.

9. Method of claim 5 wherein the composition is in liquid form.

* * * * *